US009802835B2

(12) United States Patent
Chiou et al.

(10) Patent No.: US 9,802,835 B2
(45) Date of Patent: Oct. 31, 2017

(54) METHOD FOR PRODUCING METAL CARBONATE AND CATALYST FOR PRODUCING THE SAME

(71) Applicant: TaiGreen Science Inc., Taipei (TW)

(72) Inventors: Tzung-Wen Chiou, Taipei (TW); Kuan-Fu Liu, Taipei (TW); Wen-Feng Liaw, Taipei (TW)

(73) Assignee: TAIGREEN SCIENCE INC., Taipei (TW)

( * ) Notice: Subject to any disclaimer, the term of this patent is extended or adjusted under 35 U.S.C. 154(b) by 0 days.

(21) Appl. No.: 15/067,961

(22) Filed: Mar. 11, 2016

(65) Prior Publication Data

US 2017/0217786 A1    Aug. 3, 2017

(30) Foreign Application Priority Data

Feb. 1, 2016   (TW) .............. 105103196 A

(51) Int. Cl.
| | |
|---|---|
| *C01G 49/00* | (2006.01) |
| *C07C 211/65* | (2006.01) |
| *C01D 7/00* | (2006.01) |
| *C01G 9/00* | (2006.01) |
| *B01J 31/22* | (2006.01) |
| *B01J 31/18* | (2006.01) |

(52) U.S. Cl.
CPC ........ *C01G 49/009* (2013.01); *B01J 31/1805* (2013.01); *B01J 31/22* (2013.01); *C01D 7/00* (2013.01); *C01G 9/006* (2013.01); *C07C 211/65* (2013.01)

(58) Field of Classification Search
CPC .... C01G 49/009; C01G 9/006; B01J 31/1805; B01J 31/22; C01D 7/00; C07C 211/65
USPC ....................................... 423/419.1
See application file for complete search history.

(56) References Cited

U.S. PATENT DOCUMENTS

| | | | |
|---|---|---|---|
| 1,944,415 | A | 1/1934 | Engberg |
| 2,144,299 | A | 1/1939 | Sessions et al. |
| 3,011,867 | A | 12/1961 | Welsh |
| 3,510,533 | A | 5/1970 | Maxfield |
| 4,657,752 | A | 4/1987 | Lyon |
| 5,545,789 | A | 8/1996 | Duisters et al. |
| 6,555,075 | B2 | 4/2003 | Nip |

FOREIGN PATENT DOCUMENTS

GB    1062184 B    3/1967

OTHER PUBLICATIONS

Anichina, et al., An investigation of the dissociation of complexes of triethylene tetramine with first-row metal dications by electrospray ionization tandem mass spectrometry: Remote C-C bond activation, International Journal of Mass Spectrometry 2007; 267: 256-262.*
Berto, et al., Characterization of the Bridged Hyponitrite Complex {[Fe(OEP)]2(µN2O2)}: Reactivity of Hyponitrite Complexes and Biological Relevance, Inorganic Chemistry 2014; 53: 6398-6414.*
Schneppensieper, et al., Ligand Effects on the Kinetics of the Reversible Binding of NO to Selected Aminocarboxylato Complexes of Iron(II) in Aqueous Solution, Eur. J. Inorg. Chem. 2001; 2317-2325.*
Xu, et al., A bridged di-iron porphyrin hyponitrite complex as a model for biological N2O production from hyponitrite, Nitric Oxide 2016; 52: 16-20.*
Li, Lijuan; Some Coordination Chemistry of Non-Heme Iron Nitrosyl Complexes; Comments on Inorganic Chemistry A Journal of Critical Discussion of the Current Literature; vol. 23, 2002— Issue 5, Published Sep. 14, 2010; pp. 335-353.

\* cited by examiner

*Primary Examiner* — Daniel C McCracken
(74) *Attorney, Agent, or Firm* — Muncy, Geissler, Olds & Lowe, P.C.

(57) ABSTRACT

A method for producing metal carbonate is disclosed. The method includes the following steps of providing a first mixture of metal and a catalyst containing iron, NO groups, and N-containing ligands first; then introducing carbon dioxide to the first mixture to form a second mixture and obtaining a product. The method described here can improve the yield and decrease the cost of metal carbonate production.

18 Claims, 1 Drawing Sheet

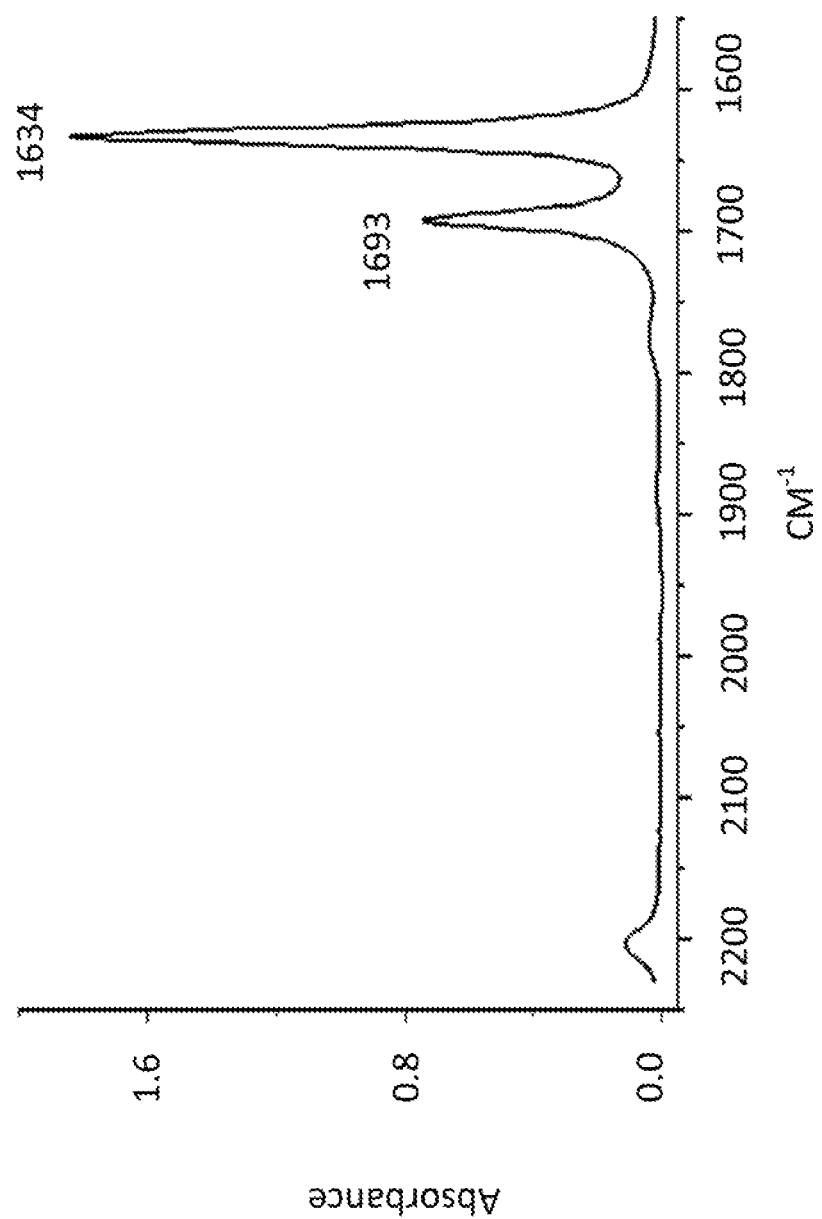

METHOD FOR PRODUCING METAL CARBONATE AND CATALYST FOR PRODUCING THE SAME

CROSS REFERENCE TO RELATED APPLICATION

This application claims the benefits of the Taiwan Patent Application Ser. No. 105103196, filed on Feb. 1, 2016, the subject matter of which is incorporated herein by reference.

BACKGROUND OF THE INVENTION

1. Field of the Invention

The present invention relates to a method for producing carbonate, more particularly, to a method for producing metal carbonate.

2. Description of Related Art

Metal carbonate is an important material for industry and is widely used in medical and industrial fields. For example, zinc carbonates are used as nutrient or medicine for zinc-deficient diseases or as astringent for cosmetics. Zinc carbonates are also major components of fire-resistant compositions or absorbents for hydrogen sulfide used in petroleum cracking. Iron carbonates may also be used as absorbents for hydrogen sulfide or as additives for animal feeds.

It is known that zinc carbonates can be produced through many processes. Currently, many zinc carbonates are synthesized through the following known synthetic route (which can be seen in the description of U.S. Pat. No. 1,944,415):

$$3ZnO+2CH_3COOH+CO_2+H_2 \rightarrow ZnCO_3 \cdot Zn(OH)_2 \cdot ZnO+2CH_3COOH$$

As illustrated by the above equation, the product zinc carbonates mixed with $Zn(OH)_2$ and $ZnO$ can be obtained. However, the known processes for producing zinc carbonate or metal carbonate are complicated and energy-consuming. In addition, further product separation or purification is often required for high-purity applications.

Therefore, it is desirable to provide an improved method for producing metal carbonate to mitigate and/or obviate the aforementioned problems.

SUMMARY OF THE INVENTION

The object of the present invention is to provide a simple method for producing metal carbonate with less energy consumption and improved yield.

Another object of the present invention is to provide a simple method for producing metal carbonate at room temperature.

Another object of the present invention is to provide a compound for improving the process for producing metal carbonate.

To achieve the object, the method for producing metal carbonate of the present invention includes the following steps: (A) providing a first mixture of metal and a solution of a catalyst represented by the following formula (I):

$$(Fe(NO)_2)_2L \tag{I}$$

wherein L is a ligand represented by the following formula (II);

$$(R_1R_2)N-(CH_2)_2-N(R_3)-(CH_2)_2-N(R_4)-(CH_2)_2-N(R_5R_6) \tag{II}$$

wherein each of $R_1$, $R_2$, $R_3$, $R_4$, $R_5$, and $R_6$ is hydrogen, or $C_1$-$C_3$ alkyl independently; and (B) introducing carbon dioxide to the first mixture to form a second mixture and obtaining a product.

The compound of the present invention is represented by the following formula (I):

$$(Fe(NO)_2)_2L \tag{I}$$

wherein L is a ligand represented by the following formula (II);

$$(R_1R_2)N-(CH_2)_2-N(R_3)-(CH_2)_2-N(R_4)-(CH_2)_2-N(R_5R_6) \tag{II}$$

wherein each of $R_1$, $R_2$, $R_3$, $R_4$, $R_5$, and $R_6$ is hydrogen, or $C_1$-$C_3$ alkyl, independently.

$R_1$ and $R_2$ of L of the present invention can be the same or different. Preferably, $R_1$ and $R_2$ of L are the same. $R_3$ and $R_4$ of L of the present invention can be the same or different. Preferably, $R_3$ and $R_4$ of L are the same. $R_5$ and $R_6$ of L of the present invention can be the same or different. Preferably, $R_5$ and $R_6$ are the same. Each of $R_1$, $R_2$, $R_3$, $R_4$, $R_5$, and $R_6$ of L the present invention, as illustrated above, is hydrogen, or $C_1$-$C_3$ alkyl, independently. Preferably, $R_1$, $R_2$, $R_3$, $R_4$, $R_5$, and $R_6$ of L are hydrogen, or methyl. More preferably, L is 1,1,4,7,10,10-hexamethyltriethylenetetramine, or triethylenetetramine. The metal carbonate of the present invention is not limited. Preferably, the metal of the metal carbonate of the present invention is Na, Mg, Zn, Fe, or the combination thereof. The compound of the present invention can be used as a catalyst for reactions. Preferably, the compound of the present invention is used as a catalyst for the reaction for producing metal carbonate. More preferably, the compound of the present invention is used as a catalyst for the reaction for producing sodium carbonate, magnesium carbonate, zinc carbonate, iron carbonate, or the combination thereof.

The method of the present invention can optionally further include step (C) drying or filtering the second mixture to collect the product of step (B). The temperature for performing the method of the present invention is not limited. Preferably, the method of the present invention is performed at a temperature under 250° C. More preferably, the method of the present invention is performed at room temperature. The solution of the method of the present invention in step (A) is not limited. Preferably, the solution is an organic solution or an aqueous solution.

The method of the present invention can be completed using the compound represented by formula (I). The general reaction of the method of the present invention can be described by the following reaction formula (III):

$$2CO_{2(g)} + M \xrightarrow[H_2O/R.T.]{catalyst} MCO_{3(g)} + CO_{(g)} \tag{III}$$

wherein M is metal.

Through the assistance of the compound of the present invention described above, metal carbonates can be synthesized in a simple way with less energy consumption and improved yield.

Other objects, advantages, and novel features of the present invention will become more apparent from the following detailed description when taken in conjunction with the accompanying drawings.

BRIEF DESCRIPTION OF THE DRAWINGS

The figure is an IR spectrum of [(HMTETA)(Fe(NO)$_2$)$_2$] Complex of Example 1-1.

DETAILED DESCRIPTION OF THE PREFERRED EMBODIMENT

Example 1-1

Synthesis of [(HMTETA)(Fe(NO)$_2$)$_2$] Complex (HMTETA: 1,1,4,7,10, 10-Hexamethyltriethylenetetramine)

Compounds [Na][NO$_2$] (10.0 mmol, 0.690 g) and 18-crown-6-ether (10.0 mmol, 2.643 g) were dissolved in THF in the 50 mL Schlenk flask, and the commercial [Fe(CO)$_5$] (10.0 mmol, 1.348 mL) was added into the THF mixture solution at 0° C. The resulting solution was stirred at ambient temperature overnight. The reaction was monitored with FTIR. IR spectrum (IR 1983 m, 1877 s ($\upsilon_{CO}$), 1647 m ($\upsilon_{NO}$)) cm$^{-1}$ (THF)) was assigned to the formation of [Na-18-crown-6-ether][Fe(CO)$_3$(NO)]. Hexane was added to precipitate the yellow solid [Na-18-crown-6-ether][Fe(CO)$_3$(NO)] (3.885 g, 85%).

[18-crown-6-ether-Na][Fe(CO)$_3$)NO] (1.828 g, 3 mmol) and [NO][BF$_4$] (nitrosonium tetrafluoroborate) (0.467 g, 3 mmol) in a 50 mL Schlenk flask were weighted. THF (~20 mL) was then added. After reacting during mixing at room temperature for approximately 20 mins, Fe(CO)$_2$(NO)$_2$ (IR: 2088s, 2037s, (v$_{CO}$), 1808s, 1760s (v$_{NO}$) cm$^{-1}$ (THF)) was produced. 1,1,4,7,10, 10-Hexamethyltriethylenetetramine (HMTETA) (0.408 mL, 1.5 mmol) was then added to the reaction solution using a plastic syringe. After reacting during mixing for 30 mins, IR vibrational frequency of the reaction solution was measured at 1693s, 1634s cm$^{-1}$ (v$_{No}$) (THF). [(HMTETA)(Fe(NO)$_2$)$_2$] was speculated to have formed. Hexane was then added to the upper layer (volume ratio of hexane:THF was approximately 4:1). Dark brown crystals were obtained after the reaction solution was left to stand for approximately 3 days. The structure of the dark brown crystals obtained was then identified using x-ray single crystal diffraction analysis and IR (v$_{No}$): 1693s, 1634 cm$^{-1}$ (THF) (shown in FIG. 1).

Example 1-2

Synthesis of [(TETA)(Fe(NO)$_2$)$_2$] Complex (TETA: triethylenetetramine)

THF solution of Fe(CO)$_2$(NO)$_2$ (prepared from the reaction of [18-crown-6-ether-Na][Fe(CO)$_3$(NO)] (1.828 g, 3 mmol) and [NO][BF$_4$] (0.467 g, 3 mmol) in THF (20 mL)) and triethylenetetramine (TETA) (0.223 mL, 1.5 mmol) was stirred at ambient temperature for 30 minutes. IR v$_{NO}$ frequencies of 1688, 1630 cm$^{-1}$ indicate the formation of [(TETA)(Fe(NO)$_2$)$_2$]. Then addition of hexane into the reaction solution led to dark-brown semi-solid [(TETA)(Fe(NO)$_2$)$_2$] (details described in Experimental Section). IR v$_{NO}$: 1688, 1630 cm$^{-1}$ (THF).

Example 2

Synthesis of Carbonate Complex

Sodium metal strip (0.069 g, 3 mmol) in a 100 mL Schlenk flask was weighted. The reaction flask was next put in a glovebox filled with nitrogen gas. Iron metal complex [(HMTETA)(Fe(NO)$_2$)$_2$] (0.0138 g, 0.03 mmol) was weighted in the glovebox. THF (~20 mL) was then added followed by supplying carbon dioxide gas (~73.5 mL, 3 mmol) into the glovebox. After reacting during mixing for approximately 3 days in a sealed environment with no ventilation, white colored sodium carbonate (Na$_2$CO$_3$) was produced in the reaction flask. Gas at the headspace was analyzed using gas chromatography 3 days later. A peak of carbon monoxide was detected (reaction formula 1). THF was then removed, water was added, and the solution was filtered and left to stand for several days. Until water had evaporated naturally, sodium carbonate (Na$_2$CO$_3$) crystals (0.144 g, 90% yield) were obtained. The structure of the sodium carbonate (Na$_2$CO$_3$) crystals was then identified using x-ray single crystal diffraction analysis.

Example 3-1 to 3-4

Zinc metal powder (0.6538 g, 10 mmol) in a 500 mL glass reaction flask was weighted in air. The reaction flask was next put in a glovebox filled with nitrogen gas. [(HMTETA)(Fe(NO)$_2$)$_2$] complex (0.046 g, 0.1 mmol) was weighted and loaded into the flask in the glovebox. Aqueous solvent (~100 mL) was then added. Carbon dioxide gas (490 mL, 20 mmol) was bubbled into the reaction aqueous solution at room temperature and pressure. After reacting during mixing at room temperature and pressure for 15 hrs, pure white colored zinc carbonate (ZnCO$_3$) was produced in the reaction flask. The calculated yield was 1.125 g (89.7%) (Table 1, Entry 1). Gas at the headspace was analyzed using gas chromatography. A peak of carbon monoxide was detected.

Next, zinc carbonates (ZnCO$_3$) from reactions using different ratios of Zn: [(HMTETA)(Fe(NO)$_2$)$_2$] complex were produced using the same experiment procedure described above (Table 1). As the zinc metal ratio increased, the supplying ratio of carbon dioxide also increased. Reaction was deemed to be completed until the product in the reaction flask had all turned to white colored zinc carbonate. The white colored zinc carbonates were then identified by FTIR (IR: v$_{CO3}$ 1445 cm$^{-1}$ (KBr)) and elemental analysis (Calc. C 9.58%, found C, 9.55%).

TABLE 1

| Entry | Metal | Solvent | Zn:[(HMTETA)(Fe(NO)$_2$)$_2$] | ZnCO$_3$ (Yield) |
| --- | --- | --- | --- | --- |
| 3-1 | Zn | H$_2$O | 10 mmol:0.1 mmol | 89.7% |
| 3-2 | Zn | H$_2$O | 50 mmol:0.1 mmol | 91.24% |
| 3-3 | Zn | H$_2$O | 0.1 mol:0.1 mmol | 96.3% |
| 3-4 | Zn | H$_2$O | 0.5 mol:0.1 mmol | 94.8% |

Example 4

Complex [(HMTETA)(Fe(NO)$_2$)$_2$] (0.046 g, 0.1 mmol) and magnesium metal (0.243 g, 10 mmol) were loaded in the 500 mL flask and dissolved in H$_2$O (100 mL). CO$_2$ gas (490 mL, 20 mmol) was then injected into the H$_2$O solution of complexes Mg-[(HMTETA)(Fe(NO)$_2$)$_2$] with a gastight syringe at ambient temperature. After the heterogeneous mixture solution was stirred at ambient temperature for 20 hours, the white solid magnesium carbonate (MgCO$_3$) precipitated from the H$_2$O solution accompanied by release of CO characterized by GC (gas chromatography) analysis of gas samples in the headspace. The white precipitate was collected through filtering and dried to yield pure MgCO$_3$ (yield 0.674 g, 80%). IR $v_{NO}$ stretching frequency 1486, 1424 cm$^{-1}$ (KBr) suggests the formation of $MgCO_3$.

Example 5

Iron metal (0.559 g, 10 mmol) and complex [(HMTETA)(Fe(NO)$_2$)$_2$] (0.046 g, 0 1 mmol) were loaded in the 500 mL flask and dissolved in $H_2O$ (100 mL). $CO_2$ gas (490 mL, 20 mmol) was then injected into the $H_2O$ solution of complexes Fe-[(HMTETA)(Fe(NO)$_2$)$_2$] with a gastight syringe at ambient temperature. After the heterogeneous mixture solution was stirred at ambient temperature for 72 hours, the red-brown solid iron carbonate (FeCO$_3$) precipitated from the $H_2O$ solution accompanied by release of CO characterized by GC (gas chromatography) analysis of gas samples in the headspace. The red-brown precipitate was collected through filtering and dried to yield pure FeCO$_3$ (yield 0.928 g, 80%). IR $V_{NO}$ stretching frequency 1419 cm$^{-1}$ (KBr) suggests the formation of FeCO$_3$.

In the present invention, metal carbonates can be produced at room temperature and under the pressure of about 1 atm. by the method of the present invention without the need of additional electrical or photo energies. Moreover, the reaction of the method of the present invention can be achieved in organic phase or aqueous solutions in the presence of the catalyst as described above. Hence, the method of the present invention is simple, energy-saving, and cheap compared to that of the conventional methods.

Although the present invention has been explained in relation to its preferred embodiment, it is to be understood that many other possible modifications and variations can be made without departing from the spirit and scope of the present invention as hereinafter claimed.

What is claimed is:

1. A method for producing metal carbonate, comprising following steps:
   (A) providing a first mixture of metal and a solution of a catalyst represented by the following formula (I):

$$(Fe(NO)_2)_2L \tag{I}$$

wherein L is a ligand represented by the following formula (II);

$$(R_1R_2)N\text{---}(CH_2)_2\text{---}N(R_3)\text{---}(CH_2)_2\text{---}N(R_4)\text{---}(CH_2)_2\text{---}N(R_5R_6) \tag{II}$$

wherein each of $R_1$, $R_2$, $R_3$, $R_4$, $R_5$, and $R_6$, independently is hydrogen, or $C_1$-$C_3$ alkyl; and
   (B) introducing carbon dioxide to the first mixture to form a second mixture and obtaining a product.

2. The method of claim 1, further comprising step (C) drying or filtering the second mixture to collect the product of step (B).

3. The method of claim 1, wherein the metal is Na, Mg, Zn, Fe, or the combination thereof.

4. The method of claim 1, wherein the step (B) is performed at room temperature.

5. The method of claim 1, wherein $R_1$ and $R_2$ are the same.

6. The method of claim 1, wherein $R_3$ and $R_4$ are the same.

7. The method of claim 1, wherein $R_5$ and $R_6$ are the same.

8. The method of claim 1, wherein $R_1$, $R_2$, $R_3$, $R_4$, $R_5$, and $R_6$ are hydrogen, or methyl.

9. The method of claim 1, wherein L is 1,1,4,7,10,10-hexamethyltriethylenetetramine.

10. The method of claim 1, wherein L is triethylenetetramine.

11. The method of claim 1, wherein the solution of a catalyst in step (A) is an aqueous solution, or organic solution.

12. A compound represented by the following formula (I):

$$(Fe(NO)_2)_2L \tag{I}$$

wherein L is a ligand represented by the following formula (II);

$$(R_1R_2)N\text{---}(CH_2)_2\text{---}N(R_3)\text{---}(CH_2)_2\text{---}N(R_4)\text{---}(CH_2)_2\text{---}N(R_5R_6) \tag{II}$$

wherein each of $R_1$, $R_2$, $R_3$, $R_4$, $R_5$, and $R_6$, independently is hydrogen, or $C_1$-$C_3$ alkyl.

13. The compound of claim 12, wherein $R_1$ and $R_2$ are the same.

14. The compound of claim 12, wherein $R_5$ and $R_6$ are the same.

15. The compound of claim 12, wherein $R_3$ and $R_4$ are the same.

16. The compound of claim 12, wherein $R_1$, $R_2$, $R_3$, $R_4$, $R_5$, and $R_6$ are hydrogen, or methyl.

17. The compound of claim 12, wherein L is 1,1,4,7,10,10-hexamethyltriethylenetetramine.

18. The compound of claim 12, wherein L is triethylenetetramine.

* * * * *